(12) United States Patent
Fujita et al.

(10) Patent No.: US 7,863,461 B2
(45) Date of Patent: Jan. 4, 2011

(54) EPOXY COMPOUNDS AND METHOD FOR PRODUCTION OF THE SAME

(75) Inventors: Toshio Fujita, Kawasaki (JP); Yuji Kobayashi, Kawasaki (JP); Hiroshi Uchida, Kawasaki (JP); Nobutoshi Sasaki, Kawasaki (JP); Kazuhiko Sato, Tsukuba (JP); Masanori Ookoshi, Tsukuba (JP); Masao Shimizu, Tsukuba (JP)

(73) Assignees: Showa Denko K.K., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 223 days.

(21) Appl. No.: 12/301,716

(22) PCT Filed: May 17, 2007

(86) PCT No.: PCT/JP2007/060566

§ 371 (c)(1),
(2), (4) Date: Nov. 20, 2008

(87) PCT Pub. No.: WO2007/136106

PCT Pub. Date: Nov. 29, 2007

(65) Prior Publication Data

US 2009/0253915 A1  Oct. 8, 2009

(30) Foreign Application Priority Data

May 22, 2006  (JP) .............................. 2006-141549
Jun. 6, 2006  (JP) .............................. 2006-157448

(51) Int. Cl.
C07F 7/02  (2006.01)
(52) U.S. Cl. ..................................... 548/406; 548/430
(58) Field of Classification Search ................. 548/406, 548/430
See application file for complete search history.

(56) References Cited

U.S. PATENT DOCUMENTS 3,455,949 A  7/1969  Porret et al.
6,080,872 A  6/2000  Pirola et al.

FOREIGN PATENT DOCUMENTS

JP  55-080430 A  6/1980

OTHER PUBLICATIONS

EP Communication, dated Jul. 22, 2009, issued in corresponding EP Application No. 07744000.6, 4 pages.
Roig et al., "Synthesis of new cycloaliphatic epoxy resins and their crosslinking," Die Makromolekulare Chemie, Feb. 1993, vol. 194, No. 2, pp. 411-419, XP000334505.

Primary Examiner—Kamal A Saeed
Assistant Examiner—Valerie Rodriguez-Garcia
(74) Attorney, Agent, or Firm—Sughrue Mion, PLLC

(57) ABSTRACT

Novel epoxy compounds having imide structures represented by general formula (I) or general formula (II) below, and having an allyl group in the same molecule, as well as a process for their production

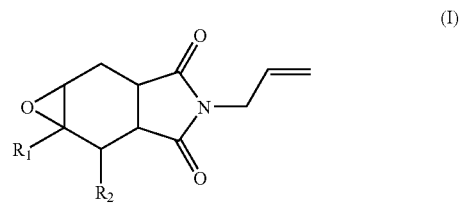

(I)

(wherein $R_1$ and $R_2$ each represent hydrogen, a C1-6 alkyl group, or a C1-4 trialkylsilyl group)

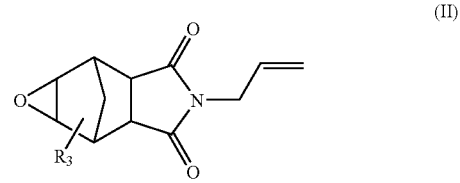

(II)

(wherein $R_3$ represents hydrogen, a C1-6 alkyl group, or a C1-4 trialkylsilyl group).

8 Claims, 2 Drawing Sheets

EPOXY COMPOUNDS AND METHOD FOR PRODUCTION OF THE SAME

TECHNICAL FIELD

The present invention relates to novel epoxy compounds that are useful as sealing materials that are used for electrical and electronic parts, molding materials, casting materials, laminating materials, composite materials, adhesives and powder coatings, as well as starting materials for hydrosilylation.

BACKGROUND ART

Epoxy compounds are used in a wide range of fields as sealing materials for electrical and electronic parts, molding materials, casting materials, laminating materials, composite materials, adhesives and powder coatings, because their curing with various curing agents yields cured products with excellent mechanical properties, humidity resistance and electrical properties.

With continuing advances in technology, increasingly higher performance is being demanded of epoxy compounds in terms of their heat resistance, for example. Improvement in heat resistance by using N-(2,3-epoxypropyl)perhydro-4,5-epoxyphthalimide, which has an imide structure, has already been proposed (R. Antoni et al., Makromol. Chem., 194, 411 (1993)), but since the process described therein employs epichlorhydrin during the production steps for the intermediate it is impossible to avoid inclusion of halogen residue in the final product, and therefore the process is not desirable as a process for production of products that are intended to be used as electronic materials requiring minimal halogen residue. Also, while imide epoxy compounds with identical allyl groups in the molecule are preferred for compositing with other resin compounds and the like, such epoxy compounds have glycidyl groups and therefore cannot be applied for useful and important industrial reactions such as hydrosilylation.

Similar imide backbone-containing epoxy compounds have also been proposed (see Japanese Unexamined Patent Publication No. 2000-17048), but because they also include aromatic rings, they are unsuitable for purposes such as LED sealing materials. It has therefore been a highly desirable goal in the industry to solve these problems by providing allyl group-containing alicyclic epoximide compounds.

DISCLOSURE OF INVENTION

The present invention provides novel epoxy compounds that are useful as sealing materials, molding materials, casting materials, laminating materials, composite materials, adhesives and powder coatings, as well as starting materials for hydrosilylation, that are used for electrical and electronic parts.

As a result of much diligent research directed toward solving the problems mentioned above, the present inventors have discovered novel epoxy compounds having imide structures represented by general formula (I) and general formula (II) below, and having an allyl group in the same molecule. The present invention relates to the following [1] to [8].

[1] An epoxy compound represented by the following general formula (I):

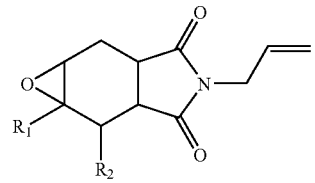

(wherein $R_1$ and $R_2$ each represents hydrogen, a C1-6 alkyl group, or a C1-4 trialkylsilyl group).

[2] An epoxy compound according to [1] above, wherein in general formula (I), $R_1$ and $R_2$ are hydrogen, or $R_1$ is any one from among methyl, ethyl, propyl, isopropyl, tertiary butyl, trimethylsilyl, triethylsilyl and tertiary butyldimethylsilyl groups while $R_2$ is hydrogen, or $R_1$ is hydrogen while $R_2$ is any one from among methyl, ethyl, propyl, isopropyl, tertiary butyl, trimethylsilyl, triethylsilyl and tertiary butyldimethylsilyl groups.

[3] An epoxy compound represented by the following general formula (II):

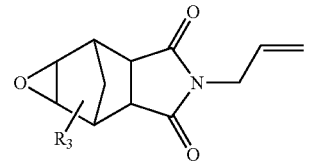

(wherein $R_3$ is hydrogen, a C1-6 alkyl group, or a C1-4 trialkylsilyl group).

[4] An epoxy compound according to [3] above, wherein in general formula (II), $R_3$ is hydrogen or $R_3$ is any one from among methyl, ethyl, propyl, isopropyl, tertiary butyl, trimethylsilyl, triethylsilyl and tertiary butyldimethylsilyl groups.

[5] A process for production of an epoxy compound according to [1] or [2] above, characterized by reacting a peroxide with an alicyclic olefin compound represented by the following general formula (III):

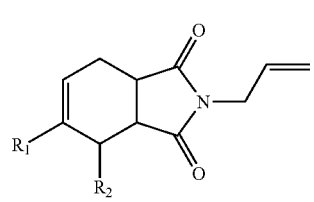

(wherein $R_1$ and $R_2$ each represents hydrogen, a C1-6 alkyl group, or a C1-4 trialkylsilyl group).

[6] A process for production of an epoxy compound according to [5] above, wherein in general formula (III), $R_1$ and $R_2$ are hydrogen, or $R_1$ is any one from among methyl, ethyl, propyl, isopropyl, tertiary butyl, trimethylsilyl, triethylsilyl and tertiary butyldimethylsilyl groups while $R_2$ is hydrogen, or $R_1$ is hydrogen while $R_2$ is any one of from among methyl, ethyl, propyl, isopropyl, tertiary butyl, trimethylsilyl, triethylsilyl and tertiary butyldimethylsilyl groups.

[7] A process for production of an epoxy compound according to [3] or [4] above, characterized by reacting a peroxide with an alicyclic olefin compound represented by the following general formula (IV):

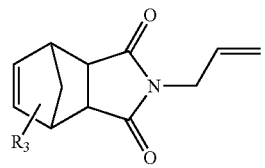

(wherein $R_3$ represents hydrogen, a C1-6 alkyl group, or a C1-4 trialkylsilyl group).

[8] A process for production of an epoxy compound according to [7] above, wherein in general formula (IV), $R_3$ is hydrogen or any one from among methyl, ethyl, propyl, isopropyl, tertiary butyl, trimethylsilyl, triethylsilyl and tertiary butyldimethylsilyl groups.

The novel epoxy compounds of the invention are useful in a wide range of fields including sealing materials, molding materials, casting materials, laminating materials, composite materials, adhesives and powder coatings that are used for electrical and electronic parts. They are also extremely useful for the purpose of enhancing the performance of known silicon resins and the like by utilizing the allyl groups for combination with other materials.

BEST MODE FOR CARRYING OUT THE INVENTION

Figure 1:
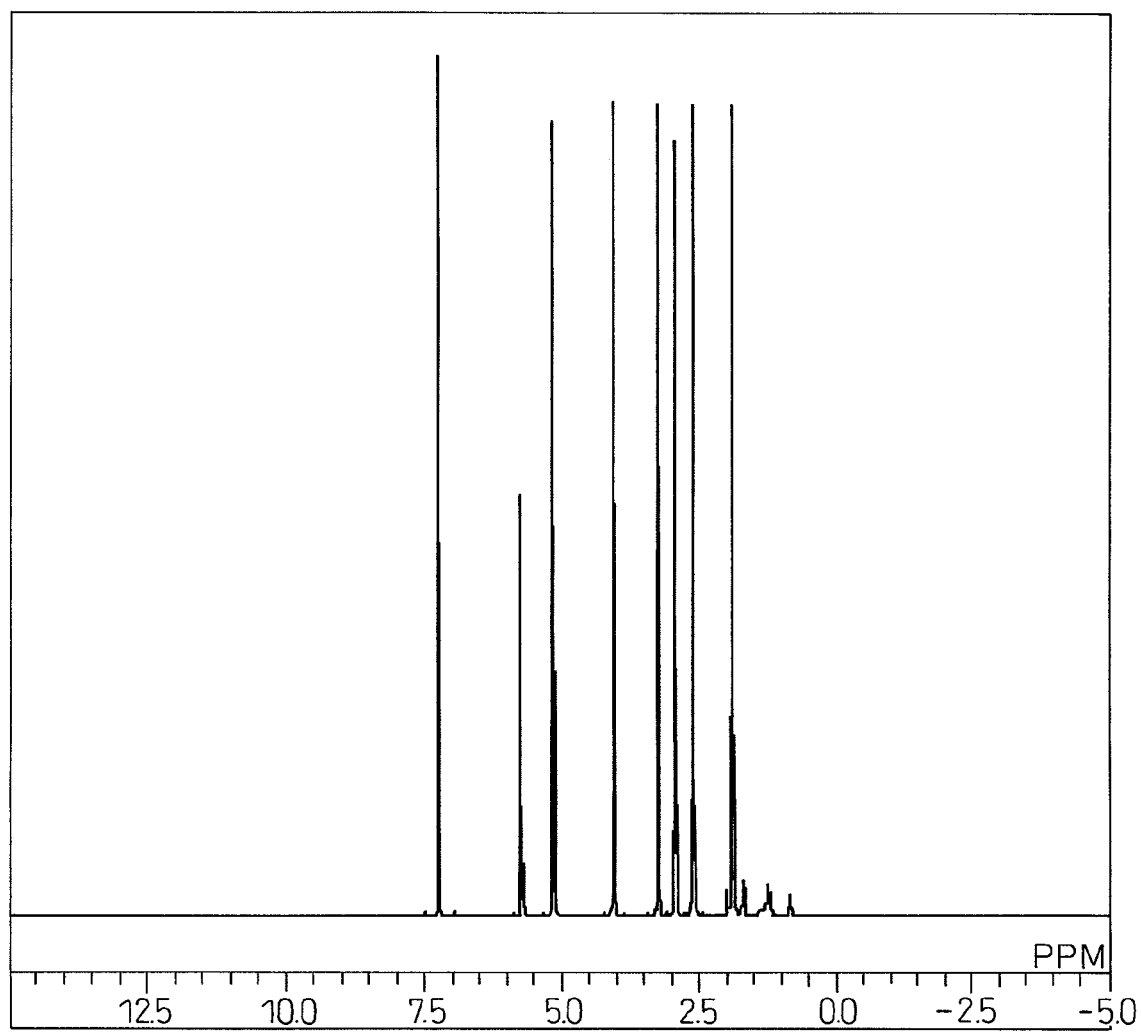
FIG. 1 is a chart showing the $^1$H-NMR spectrum for the 4,5-epoxy-N-allylcyclohexane-1,2-dicarboximide 1 obtained in Example 1.

The present invention will now be explained in greater detail.

The novel imide alicyclic epoxy compounds obtained according to the invention are represented by the following general formula (I):

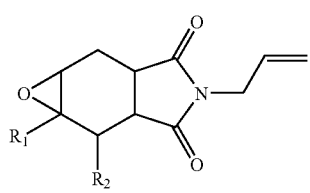

(wherein $R_1$ and $R_2$ each represents hydrogen, a C1-6 alkyl group, or a C1-4 trialkylsilyl group).

Specifically, the novel imide alicyclic epoxy compounds represented by general formula (I) may be:
4,5-epoxy-N-allylcyclohexane-1,2-dicarboximide,
3-methyl-4,5-epoxy-N-allylcyclohexane-1,2-dicarboximide,
4-methyl-4,5-epoxy-N-allylcyclohexane-1,2-dicarboximide,
3-ethyl-4,5-epoxy-N-allylcyclohexane-1,2-dicarboximide,
4-ethyl-4,5-epoxy-N-allylcyclohexane-1,2-dicarboximide,
3-propyl-4,5-epoxy-N-allylcyclohexane-1,2-dicarboximide,
4-propyl-4,5-epoxy-N-allylcyclohexane-1,2-dicarboximide,
3-isopropyl-4,5-epoxy-N-allylcyclohexane-1,2-dicarboximide,
4-isopropyl-4,5-epoxy-N-allylcyclohexane-1,2-dicarboximide,
3-butyl-4,5-epoxy-N-allylcyclohexane-1,2-dicarboximide,
4-butyl-4,5-epoxy-N-allylcyclohexane-1,2-dicarboximide,
3-isobutyl-4,5-epoxy-N-allylcyclohexane-1,2-dicarboximide,
4-isobutyl-4,5-epoxy-N-allylcyclohexane-1,2-dicarboximide,
3-tertiary butyl-4,5-epoxy-N-allylcyclohexane-1,2-dicarboximide,
4-tertiary butyl-4,5-epoxy-N-allylcyclohexane-1,2-dicarboximide,
3-pentyl-4,5-epoxy-N-allylcyclohexane-1,2-dicarboximide,
4-pentyl-4,5-epoxy-N-allylcyclohexane-1,2-dicarboximide,
3-hexyl-4,5-epoxy-N-allylcyclohexane-1,2-dicarboximide,
4-hexyl-4,5-epoxy-N-allylcyclohexane-1,2-dicarboximide,
3-trimethylsilyl-4,5-epoxy-N-allylcyclohexane-1,2-dicarboximide,
4-trimethylsilyl-4,5-epoxy-N-allylcyclohexane-1,2-dicarboximide,
3-triethylsilyl-4,5-epoxy-N-allylcyclohexane-1,2-dicarboximide,
4-triethylsilyl-4,5-epoxy-N-allylcyclohexane-1,2-dicarboximide,
3-tertiary butyldimethylsilyl-4,5-epoxy-N-allylcyclohexane-1,2-dicarboximide, or
4-tertiary butyldimethylsilyl-4,5-epoxy-N-allylcyclohexane-1,2-dicarboximide.

More specifically, the novel imide alicyclic epoxy compound represented by general formula (I) may be:
4,5-epoxy-N-allylcyclohexane-1,2-dicarboximide,
3-methyl-4,5-epoxy-N-allylcyclohexane-1,2-dicarboximide,
4-methyl-4,5-epoxy-N-allylcyclohexane-1,2-dicarboximide,
3-trimethylsilyl-4,5-epoxy-N-allylcyclohexane-1,2-dicarboximide,
4-trimethylsilyl-4,5-epoxy-N-allylcyclohexane-1,2-dicarboximide,
3-tertiary butyldimethylsilyl-4,5-epoxy-N-allylcyclohexane-1,2-dicarboximide, or
4-tertiary butyldimethylsilyl-4,5-epoxy-N-allylcyclohexane-1,2-dicarboximide.

The novel imide alicyclic epoxy compounds obtained according to the invention are also represented by the following general formula (II):

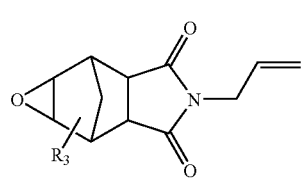

(wherein $R_3$ is hydrogen, a C1-6 alkyl group, or a C1-4 trialkylsilyl group).

Specifically, the novel imide alicyclic epoxy compounds represented by general formula (II) may be:
N-allyl-5,6-epoxybicyclo[2.2.1]heptane-2,3-dicarboximide,
N-allyl-5,6-epoxy-4-methylbicyclo[2.2.1]heptane-2,3-dicarboximide,
N-allyl-5,6-epoxy-4-ethylbicyclo[2.2.1]heptane-2,3-dicarboximide,
N-allyl-5,6-epoxy-4-propylbicyclo[2.2.1]heptane-2,3-dicarboximide,
N-allyl-5,6-epoxy-4-isopropylbicyclo[2.2.1]heptane-2,3-dicarboximide,
N-allyl-5,6-epoxy-4-butylbicyclo[2.2.1]heptane-2,3-dicarboximide,
N-allyl-5,6-epoxy-4-isobutylbicyclo[2.2.1]heptane-2,3-dicarboximide,
N-allyl-5,6-epoxy-4-tertiary butylbicyclo[2.2.1]heptane-2,3-dicarboximide,
N-allyl-5,6-epoxy-4-pentylbicyclo[2.2.1]heptane-2,3-dicarboximide,
N-allyl-5,6-epoxy-4-hexylbicyclo[2.2.1]heptane-2,3-dicarboximide,
N-allyl-5,6-epoxy-4-trimethylsilylbicyclo[2.2.1]heptane-2,3-dicarboximide,
N-allyl-5,6-epoxy-4-triethylsilylbicyclo[2.2.1]heptane-2,3-dicarboximide,
N-allyl-5,6-epoxy-4-tertiary butyldimethylsilylbicyclo[2.2.1]heptane-2,3-dicarboximide,
N-allyl-5,6-epoxy-5-methylbicyclo[2.2.1]heptane-2,3-dicarboximide,
N-allyl-5,6-epoxy-5-ethylbicyclo[2.2.1]heptane-2,3-dicarboximide,
N-allyl-5,6-epoxy-5-propylbicyclo[2.2.1]heptane-2,3-dicarboximide,
N-allyl-5,6-epoxy-5-isopropylbicyclo[2.2.1]heptane-2,3-dicarboximide,
N-allyl-5,6-epoxy-5-butylbicyclo[2.2.1]heptane-2,3-dicarboximide,
N-allyl-5,6-epoxy-5-isobutylbicyclo[2.2.1]heptane-2,3-dicarboximide,
N-allyl-5,6-epoxy-5-tertiary butylbicyclo[2.2.1]heptane-2,3-dicarboximide,
N-allyl-5,6-epoxy-5-pentylbicyclo[2.2.1]heptane-2,3-dicarboximide,
N-allyl-5,6-epoxy-5-hexylbicyclo[2.2.1]heptane-2,3-dicarboximide,
N-allyl-5,6-epoxy-5-trimethylsilylbicyclo[2.2.1]heptane-2,3-dicarboximide,
N-allyl-5,6-epoxy-5-triethylsilylbicyclo[2.2.1]heptane-2,3-dicarboximide,
N-allyl-5,6-epoxy-5-tertiary butyldimethylsilylbicyclo[2.2.1]heptane-2,3-dicarboximide,
N-allyl-5,6-epoxy-7-methylbicyclo[2.2.1]heptane-2,3-dicarboximide,
N-allyl-5,6-epoxy-7-ethylbicyclo[2.2.1]heptane-2,3-dicarboximide,
N-allyl-5,6-epoxy-7-propylbicyclo[2.2.1]heptane-2,3-dicarboximide,
N-allyl-5,6-epoxy-7-isopropylbicyclo[2.2.1]heptane-2,3-dicarboximide,
N-allyl-5,6-epoxy-7-butylbicyclo[2.2.1]heptane-2,3-dicarboximide,
N-allyl-5,6-epoxy-7-isobutylbicyclo[2.2.1]heptane-2,3-dicarboximide,
N-allyl-5,6-epoxy-7-tertiary butylbicyclo[2.2.1]heptane-2,3-dicarboximide,
N-allyl-5,6-epoxy-7-pentylbicyclo[2.2.1]heptane-2,3-dicarboximide,
N-allyl-5,6-epoxy-7-hexylbicyclo[2.2.1]heptane-2,3-dicarboximide,
N-allyl-5,6-epoxy-7-trimethylsilylbicyclo[2.2.1]heptane-2,3-dicarboximide,
N-allyl-5,6-epoxy-7-triethylsilylbicyclo[2.2.1]heptane-2,3-dicarboximide, or
N-allyl-5,6-epoxy-7-tertiary butyldimethylsilylbicyclo[2.2.1]heptane-2,3-dicarboximide.

More specifically, the novel imide alicyclic epoxy compounds represented by general formula (II) may be:
N-allyl-5,6-epoxybicyclo[2.2.1]heptane-2,3-dicarboximide,
N-allyl-5,6-epoxy-4-methylbicyclo[2.2.1]heptane-2,3-dicarboximide,
N-allyl-5,6-epoxy-4-trimethylsilylbicyclo[2.2.1]heptane-2,3-dicarboximide,
N-allyl-5,6-epoxy-4-tertiary butyldimethylsilylbicyclo[2.2.1]heptane-2,3-dicarboximide,
N-allyl-5,6-epoxy-5-methylbicyclo[2.2.1]heptane-2,3-dicarboximide,
N-allyl-5,6-epoxy-5-trimethylsilylbicyclo[2.2.1]heptane-2,3-dicarboximide,
N-allyl-5,6-epoxy-5-tertiary butyldimethylsilylbicyclo[2.2.1]heptane-2,3-dicarboximide,
N-allyl-5,6-epoxy-7-methylbicyclo[2.2.1]heptane-2,3-dicarboximide,
N-allyl-5,6-epoxy-7-trimethylsilylbicyclo[2.2.1]heptane-2,3-dicarboximide, or
N-allyl-5,6-epoxy-7-tertiary butyldimethylsilylbicyclo[2.2.1]heptane-2,3-dicarboximide.

The aforementioned novel imide alicyclic epoxy compounds can be produced by oxidative reaction of an alicyclic olefinimide compound represented by the following general formula (III) with an appropriate oxidizing agent.

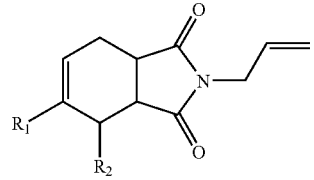

(III)

(wherein $R_1$ and $R_2$ each represents hydrogen, a C1-6 alkyl group, or a C1-4 trialkylsilyl group)

Specifically, the alicyclic olefinimide compounds represented by general formula (III) may be:
N-allyl-4-cyclohexene-1,2-dicarboximide,
N-allyl-3-methyl-4-cyclohexene-1,2-dicarboximide,
N-allyl-4-methyl-4-cyclohexene-1,2-dicarboximide,
N-allyl-3-ethyl-4-cyclohexene-1,2-dicarboximide,
N-allyl-4-ethyl-4-cyclohexene-1,2-dicarboximide,
N-allyl-3-propyl-4-cyclohexene-1,2-dicarboximide,
N-allyl-4-propyl-4-cyclohexene-1,2-dicarboximide,
N-allyl-3-isopropyl-4-cyclohexene-1,2-dicarboximide,
N-allyl-4-isopropyl-4-cyclohexene-1,2-dicarboximide,
N-allyl-3-butyl-4-cyclohexene-1,2-dicarboximide,
N-allyl-4-butyl-4-cyclohexene-1,2-dicarboximide,
N-allyl-3-isobutyl-4-cyclohexene-1,2-dicarboximide,
N-allyl-4-isobutyl-4-cyclohexene-1,2-dicarboximide,
N-allyl-3-tertiary butyl-4-cyclohexene-1,2-dicarboximide,
N-allyl-4-tertiary butyl-4-cyclohexene-1,2-dicarboximide,
N-allyl-3-pentyl-4-cyclohexene-1,2-dicarboximide,
N-allyl-4-pentyl-4-cyclohexene-1,2-dicarboximide,
N-allyl-3-hexyl-4-cyclohexene-1,2-dicarboximide, N-allyl-4-hexyl-4-cyclohexene-1,2-dicarboximide,
N-allyl-3-trimethylsilyl-4-cyclohexene-1,2-dicarboximide,
N-allyl-4-trimethylsilyl-4-cyclohexene-1,2-dicarboximide,
N-allyl-3-triethylsilyl-4-cyclohexene-1,2-dicarboximide,
N-allyl-4-triethylsilyl-4-cyclohexene-1,2-dicarboximide,
N-allyl-3-tertiary butyldimethylsilyl-4-cyclohexene-1,2-dicarboximide, or
N-allyl-4-tertiary butyldimethylsilyl-4-cyclohexene-1,2-dicarboximide.

More specifically, the alicyclic olefinimide compound represented by general formula (III) may be:
N-allyl-4-cyclohexene-1,2-dicarboximide,
N-allyl-3-methyl-4-cyclohexene-1,2-dicarboximide,
N-allyl-4-methyl-4-cyclohexene-1,2-dicarboximide,
N-allyl-3-trimethylsilyl-4-cyclohexene-1,2-dicarboximide,
N-allyl-4-trimethylsilyl-4-cyclohexene-1,2-dicarboximide,
N-allyl-3-tertiary butyldimethylsilyl-4-cyclohexene-1,2-dicarboximide, or
N-allyl-4-tertiary butyldimethylsilyl-4-cyclohexene-1,2-dicarboximide.

The aforementioned novel imide alicyclic epoxy compounds can also be produced by oxidative reaction of an alicyclic olefinimide compound represented by the following general formula (IV) with an appropriate oxidizing agent.

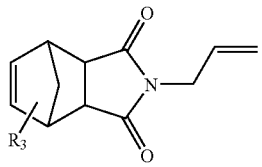

(IV)

(wherein $R_3$ represents hydrogen, a C1-6 alkyl group, or a C1-4 trialkylsilyl group)

Specifically, the alicyclic olefinimide compounds represented by general formula (IV) may be:
N-allylbicyclo[2.2.1]heptene-2,3-dicarboximide,
N-allyl-4-methylbicyclo[2.2.1]heptene-2,3-dicarboximide,
N-allyl-4-ethylbicyclo[2.2.1]heptene-2,3-dicarboximide,
N-allyl-4-propylbicyclo[2.2.1]heptene-2,3-dicarboximide,
N-allyl-4-isopropylbicyclo[2.2.1]heptene-2,3-dicarboximide,
N-allyl-4-butylbicyclo[2.2.1]heptene-2,3-dicarboximide,
N-allyl-4-isobutylbicyclo[2.2.1]heptene-2,3-dicarboximide,
N-allyl-4-tertiary butylbicyclo[2.2.1]heptene-2,3-dicarboximide,
N-allyl-4-pentylbicyclo[2.2.1]heptene-2,3-dicarboximide,
N-allyl-4-hexylbicyclo[2.2.1]heptene-2,3-dicarboximide,
N-allyl-4-trimethylsilylbicyclo[2.2.1]heptene-2,3-dicarboximide,
N-allyl-4-triethylsilylbicyclo[2.2.1]heptene-2,3-dicarboximide,
N-allyl-4-tertiary butyldimethylsilylbicyclo[2.2.1]heptene-2,3-dicarboximide,
N-allyl-5-methylbicyclo[2.2.1]heptene-2,3-dicarboximide,
N-allyl-5-ethylbicyclo[2.2.1]heptene-2,3-dicarboximide,
N-allyl-5-propylbicyclo[2.2.1]heptene-2,3-dicarboximide,
N-allyl-5-isopropylbicyclo[2.2.1]heptene-2,3-dicarboximide,
N-allyl-5-butylbicyclo[2.2.1]heptene-2,3-dicarboximide,
N-allyl-5-isobutylbicyclo[2.2.1]heptene-2,3-dicarboximide,
N-allyl-5-tertiary butylbicyclo[2.2.1]heptene-2,3-dicarboximide,
N-allyl-5-pentylbicyclo[2.2.1]heptene-2,3-dicarboximide,
N-allyl-5-hexylbicyclo[2.2.1]heptene-2,3-dicarboximide,
N-allyl-5-trimethylsilylbicyclo[2.2.1]heptene-2,3-dicarboximide,
N-allyl-5-triethylsilylbicyclo[2.2.1]heptene-2,3-dicarboximide,
N-allyl-5-tertiary butyldimethylsilylbicyclo[2.2.1]heptene-2,3-dicarboximide,
N-allyl-7-methylbicyclo[2.2.1]heptene-2,3-dicarboximide,
N-allyl-7-ethylbicyclo[2.2.1]heptene-2,3-dicarboximide,
N-allyl-7-propylbicyclo[2.2.1]heptene-2,3-dicarboximide,
N-allyl-7-isopropylbicyclo[2.2.1]heptene-2,3-dicarboximide,
N-allyl-7-butylbicyclo[2.2.1]heptene-2,3-dicarboximide,
N-allyl-7-isobutylbicyclo[2.2.1]heptene-2,3-dicarboximide,
N-allyl-7-tertiary butylbicyclo[2.2.1]heptene-2,3-dicarboximide,
N-allyl-7-pentylbicyclo[2.2.1]heptene-2,3-dicarboximide,
N-allyl-7-hexylbicyclo[2.2.1]heptene-2,3-dicarboximide,
N-allyl-7-trimethylsilylbicyclo[2.2.1]heptene-2,3-dicarboximide,
N-allyl-7-triethylsilylbicyclo[2.2.1]heptene-2,3-dicarboximide, or
N-allyl-7-tertiary butyldimethylsilylbicyclo[2.2.1]heptene-2,3-dicarboximide.

More specifically, the alicyclic olefinimide compounds represented by general formula (IV) may be:
N-allylbicyclo[2.2.1]heptene-2,3-dicarboximide,
N-allyl-4-methylbicyclo[2.2.1]heptene-2,3-dicarboximide,
N-allyl-4-trimethylsilylbicyclo[2.2.1]heptene-2,3-dicarboximide,
N-allyl-4-tertiary butyldimethylsilylbicyclo[2.2.1]heptene-2,3-dicarboximide,
N-allyl-5-methylbicyclo[2.2.1]heptene-2,3-dicarboximide,
N-allyl-5-trimethylsilylbicyclo[2.2.1]heptene-2,3-dicarboximide,
N-allyl-5-tertiary butyldimethylsilylbicyclo[2.2.1]heptene-2,3-dicarboximide,
N-allyl-7-methylbicyclo[2.2.1]heptene-2,3-dicarboximide,
N-allyl-7-trimethylsilylbicyclo[2.2.1]heptene-2,3-dicarboximide, or
N-allyl-7-tertiary butyldimethylsilylbicyclo[2.2.1]heptene-2,3-dicarboximide.

The oxidizing agents used for oxidation of alicyclic olefinimide compounds represented by general formula (III) or general formula (IV) in order to obtain alicyclic epoximide compounds represented by general formula (I) or general formula (II), respectively, may be any ones employed in the industry without exception, and as examples there may be mentioned hydrogen peroxide and alkyl peroxides such as performic acid, peracetic acid, 3-chloroperoxybenzoic acid, cumene peroxide, dimethyldioxirane and the like. Preferred oxidizing agents are hydrogen peroxide, peracetic acid and 3-chloroperoxybenzoic acid, with hydrogen peroxide and peracetic acid being even more preferred.

There are no particular restrictions on the concentration for use of hydrogen peroxide water, and reaction with olefins may occur depending on the concentration; however, for most purposes it may be selected within the range of 1-80% and preferably 20-60%.

There are also no particular restrictions on the amount of hydrogen peroxide water solution used, and reaction with olefins may occur depending on the amount of use; however, for most purposes it may be selected within the range of 0.8-10.0 equivalents and preferably 1.0-3.0 equivalents with respect to the olefins.

Oxidation reaction by hydrogen peroxide can be carried out in the presence of a quaternary ammonium hydrogensulfate and a catalytic amount of a Group 6 metal compound (molybdenum, tungsten).

As examples of quaternary ammonium hydrogensulfates there may be mentioned tetrahexylammonium hydrogensulfate, tetraoctylammonium hydrogensulfate, methyltrioctylammonium hydrogensulfate, tetrabutylammonium hydrogensulfate, ethyltrioctylammonium hydrogensulfate and cetylpyridinium hydrogensulfate, with tetrahexylammonium hydrogensulfate, tetraoctylammonium hydrogensulfate and methyltrioctylammonium hydrogensulfate being preferred. These quaternary ammonium hydrogensulfates may be used alone or in combinations of two or more.

The amount of use is selected within a range of 0.0001-10 mol % and preferably 0.01-5 mol % with respect to the olefin substrate.

When the Group 6 metal compound is molybdenum, it may be a compound that forms molybdate anion in water, such as molybdic acid, molybdenum trioxide, molybdenum trisulfide, molybdenum hexachloride, phosphomolybdic acid, ammonium molybdate, potassium molybdate dihydrate, sodium molybdate dihydrate or the like, among which molybdic acid, molybdenum trioxide and phosphomolybdic acid are preferred.

In the case of tungsten, it may be a compound that forms tungstate anion in water, such as tungstic acid, tungsten trioxide, tungsten trisulfide, tungsten hexachloride, phosphotungstic acid, ammonium tungstate, potassium tungstate dihydrate, sodium tungstate dihydrate or the like, among which tungstic acid, tungsten trioxide, phosphotungstic acid and sodium tungstate dihydrate are preferred. These Group 6 metal compounds may also be used alone or in combinations of two or more.

The amount of use is selected within a range of 0.0001-20 mol % and preferably 0.01-10 mol % with respect to the olefin substrate.

Such catalysts may also be modified by using additives such as phosphoric acid, polyphosphoric acid, aminomethylphosphonic acid and sodium phosphate.

For a production process that employs oxidative reaction with hydrogen peroxide, the reaction will normally be carried out in the range of 30-100° C. and preferably 50-90° C.

There are no particular restrictions on the concentration of acetate solution for peracetic acid, but generally it is selected in the range of 1-80% and preferably 9-40%. Also, the amount of acetate solution for peracetic acid that is used is not particularly restricted, but it may be selected in the range of 0.8-10.0 equivalents and preferably 1.0-2.0 equivalents with respect to the olefins.

The oxidation reaction with an acetate solution containing peracetic acid may be carried out without a solvent or with a solvent. The solvent may be any one that permits dissolution, and specifically there may be used hexane, heptane, octane, decane, ethyl acetate, toluene, xylene, chloroform, dichloromethane, dichloroethane, tetrachloroethane or any desired mixtures thereof as necessary, while the reaction may be carried out in air, or in an inert gas atmosphere such as nitrogen or argon.

For production by oxidation with an acetate solution of peracetic acid, the reaction will usually be carried out in the range of 30-100° C. and preferably 50-90° C.

A known process may be used as the process for production of alicyclic olefinimide compounds represented by general formula (III) and general formula (IV), as precursors of the novel epoxy compounds of the invention. For example, in a reaction to obtain N-allyl-4-cyclohexene-1,2-dicarboximide, allylamine is added dropwise to a xylene solution of 1,2,3,6-tetrahydrophthalic anhydride, and the mixture is allowed to age and is heated and circulated for dehydration reaction, the produced water produced is removed by azeotropic distillation of the xylene and water with a Dean-Stark water separator, and then the xylene solvent is removed under reduced pressure to obtain a crude product which is subsequently subjected to vacuum distillation (R. A. Schmidt, Archives of Biochemistry and Biophysics, 83, 233 (1959)).

As a separate process utilizing reaction in which N-allyl-4-cyclohexene-1,2-dicarboximide is obtained, 1,2,3,6-tetrahydrophthalic anhydride is heated to dissolution, and an excess of allylamine is added to obtain a crude product which is subsequently subjected to vacuum distillation (M. S. Newman et al., J. Am. Chem. Soc., 68, 2112 (1946)).

The solvent used for production of an alicyclic olefinimide compound represented by general formula (III) or general formula (IV) as the precursor may be xylene, or toluene, metaxylene, orthoxylene, paraxylene, mesitylene or any desired mixture thereof as necessary, while the reaction may be carried out in air or in an inert gas atmosphere such as nitrogen or argon. This reaction may also be conducted with additives such as polymerization inhibitors as well.

Any common method may be used for purification of the product, such as column chromatography or thin-layer chromatography, and specifically column chromatography employing silica gel, hydrated silica gel, alumina, active carbon, titania, zirconia or the like, and more specifically silica gel, hydrated silica gel or alumina as the filler. The process used for purification may be distillation, and specifically vacuum distillation or molecular distillation.

The invention can thus provide alicyclic epoximide compounds containing allyl groups.

The present invention will now be described in greater detail by examples, with the understanding that the invention is not limited to these examples.

EXAMPLE 1

In a 200 mL separable flask equipped with a stirrer, dropping funnel and ice bath there were charged 16.98 g of 1,2,3,6-tetrahydrophthalic anhydride and 130 mL of toluene. To this there was added dropwise a total of 11.42 g of allylamine over a period of 40 minutes using a dropping funnel in a nitrogen atmosphere, and after aging for 30 minutes, a Dean-Stark water separator was mounted on the separable flask and an oil bath kept at 145° C. was used for heating and circulation for 3 hours while removing the captured water, upon which the mixture was allowed to stand overnight for cooling to room temperature.

A rotary evaporator was used to remove the toluene solvent from the contents of the flask to obtain 19.21 g of an N-allyl-4-cyclohexene-1,2-dicarboximide crude product. It was then purified by vacuum distillation to obtain 15.26 g of pure N-allyl-4-cyclohexene-1,2-dicarboximide as a colorless transparent liquid.

Figure 2:
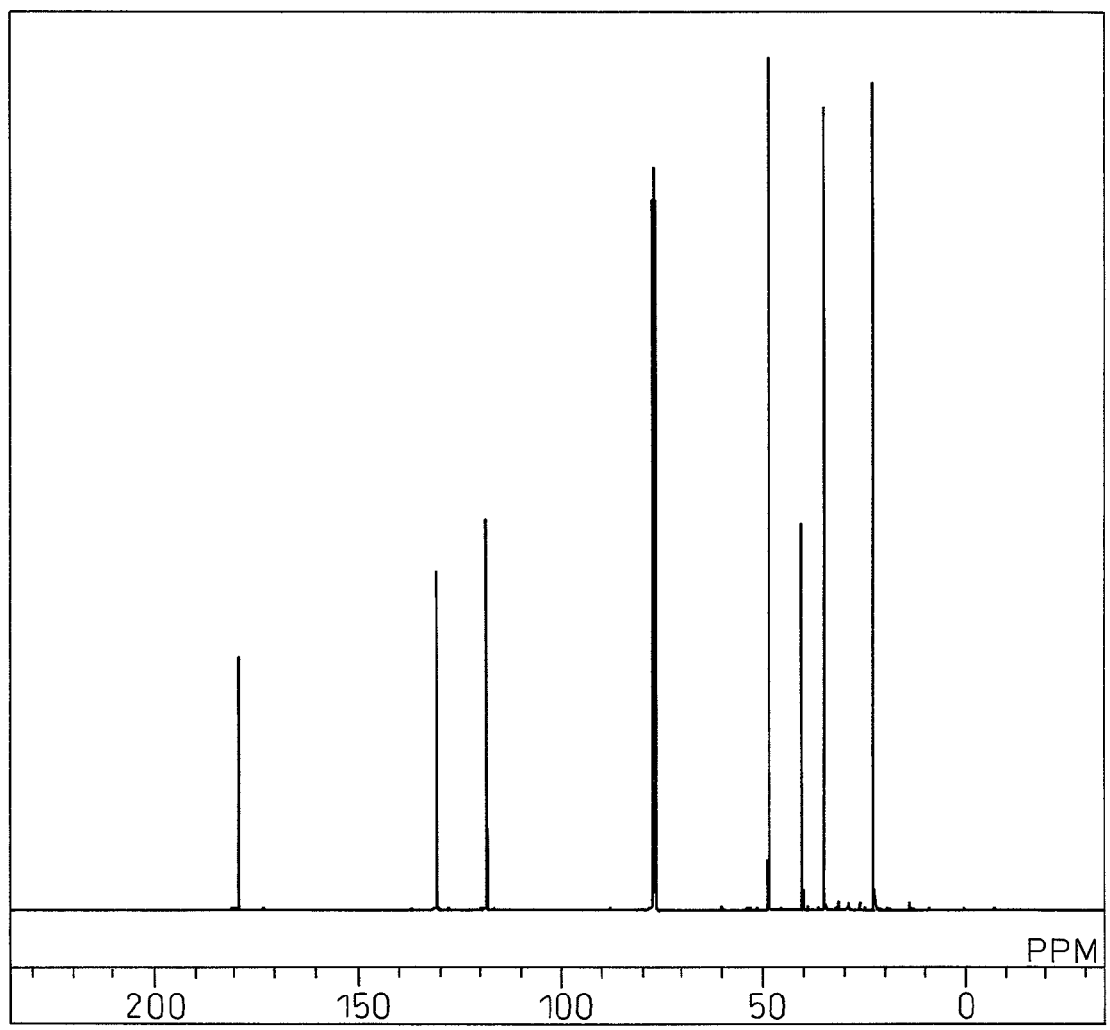
FIG. 2 is a chart showing the $^{13}$C-NMR spectrum for the 4,5-epoxy-N-allylcyclohexane-1,2-dicarboximide 1 obtained in Example 1.

In a 50 mL three-necked flask equipped with stirrer, dropping funnel and Dimroth condenser tube there were charged 5.15 g of N-allyl-4-cyclohexene-1,2-dicarboximide, 0.23 g of methyltrioctylammonium hydrogensulfate, 0.22 g of sodium tungstate dihydrate and 0.03 g of aminomethylphosphonic acid. The mixture was heated using an oil bath kept at 90° C., and after adding 4 ml of 30% hydrogen peroxide water dropwise over a period of 30 minutes through a dropping funnel, the mixture was aged for 4 hours. It was then cooled in an ice bath, and after removing the excess hydrogen peroxide with 15 mL of saturated aqueous sodium thiosulfate, extraction was performed 5 times with 10 mL of ethyl acetate. The obtained ethyl acetate solution was dried overnight over anhydrous sodium sulfate, a rotary evaporator was used to remove the ethyl acetate solvent to obtain 3.21 g of a crude product of 4,5-epoxy-N-allylcyclohexane-1,2-dicarboximide, and then purification was performed by chromatography with a column packed with 25% hydrated silica gel. Structural isomers of 4,5-epoxy-N-allylcyclohexane-1,2-dicarboximide exist due to the epoxy group, and of these there were obtained 0.72 g of 4,5-epoxy-N-allylcyclohexane-1,2-dicarboximide 1 and 0.56 g of 4,5-epoxy-N-allylcyclohexane-1,2-dicarboximide 2. An AL-400 nuclear magnetic resonance apparatus by JEOL Corp. was used to measure the $^1$H-NMR and $^{13}$C-NMR spectra of the 4,5-epoxy-N-allylcyclohexane-1,2-dicarboximide 1 in a heavy chloroform solvent, thus allowing confirmation of the structure. The $^1$H-NMR and $^{13}$C-NMR spectra of the 4,5-epoxy-N-allylcyclohexane-1,2-dicarboximide 1 are shown in FIGS. 1 and 2, respectively, and the $^1$H-NMR integral values of the 4,5-epoxy-N-allylcyclohexane-1,2-dicarboximide 1 are shown in Table 1 below.

TABLE 1

| Chemical shift (ppm) | Integral |
| --- | --- |
| 1.8-2.0 | 2.0 |
| 2.5-2.6 | 2.0 |
| 2.8-3.0 | 2.0 |
| 3.2-3.4 | 2.0 |
| 5.0-5.3 | 2.0 |
| 5.6-5.8 | 1.0 |

EXAMPLE 2

The same procedure was carried out as in Example 1 except for using 10.0 g of N-allyl-4-cyclohexene-1,2-dicarboximide, to finally obtain 4.3 g of a mixture of 4,5-epoxy-N-allylcyclohexane-1,2-dicarboximide 1 and 4,5-epoxy-N-allylcyclohexane-1,2-dicarboximide 2.

EXAMPLE 3

In a 200 mL three-necked flask equipped with a stirrer and dropping funnel there were charged 19.87 g of N-allyl-4-cyclohexene-1,2-dicarboximide and 20 mL of ethyl acetate. The mixture was heated using an oil bath kept at 60° C., and after adding 30.46 g of 40% peracetic acid dropwise through a dropping funnel over a period of 45 minutes, the mixture was aged for 1 hour. The temperature of the oil bath was then raised to 70° C. and aging was continued for 1 hour. It was then cooled in an ice bath, and after removing the excess peracetic acid with 15 mL of saturated aqueous sodium thiosulfate, extraction was performed 3 times with 25 mL of ethyl acetate. The obtained ethyl acetate solution was dried overnight over anhydrous sodium sulfate, and a rotary evaporator was used to remove the ethyl acetate solvent to obtain 12.8 g of a crude product of 4,5-epoxy-N-allylcyclohexane-1,2-dicarboximide.

EXAMPLE 4

The same procedure was carried out as in Example 1 except for using 15.0 g of 3-methyl-1,2,3,6-tetrahydrophthalimide, to finally obtain 11.6 g of 3-methyl-4,5-epoxy-N-allylcyclohexane-1,2-dicarboximide as an isomeric mixture.

EXAMPLE 5

The same procedure was carried out as in Example 1 except for using 30.5 g of methyl-5-norbornane-2,3-dicarboxylic anhydride, to finally obtain 24.3 g of N-allyl-5,6-epoxy-7-methylbicyclo[2.2.1]heptane-2,3-dicarboximide as an isomeric mixture.

INDUSTRIAL APPLICABILITY

The novel epoxy compounds of the invention are useful in a wide range of fields including sealing materials that are used for electrical and electronic parts, molding materials, casting materials, laminating materials, composite materials, adhesives and powder coatings. They are also extremely useful for the purpose of enhancing the performance of known silicon resins and the like by utilizing the allyl groups for combination with other materials.

The invention claimed is:

1. An epoxy compound of formula (I):

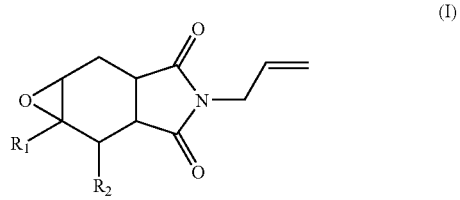

(wherein $R_1$ and $R_2$ each represents hydrogen, a C1-6 alkyl group, or a C1-4 trialkylsilyl group).

2. The epoxy compound according to claim 1, wherein in formula (I), $R_1$ and $R_2$ are hydrogen, or $R_1$ is any one from among methyl, ethyl, propyl, isopropyl, tertiary butyl, trimethylsilyl, triethylsilyl and tertiary butyldimethylsilyl groups while $R_2$ is hydrogen, or $R_1$ is hydrogen while $R_2$ is any one of from among methyl, ethyl, propyl, isopropyl, tertiary butyl, trimethylsilyl, triethylsilyl and tertiary butyldimethylsilyl groups.

3. An epoxy compound of formula (II):

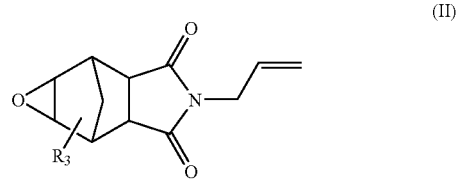

(wherein $R_3$ is hydrogen, a C1-6 alkyl group, or a C1-4 trialkylsilyl group).

4. The epoxy compound according to claim 3, wherein in formula (II), $R_3$ is hydrogen or $R_3$ is any one from among methyl, ethyl, propyl, isopropyl, tertiary butyl, trimethylsilyl, triethylsilyl and tertiary butyldimethylsilyl groups.

5. A process for production of an epoxy compound of claim 1 or 2, characterized by reacting a peroxide with an alicyclic olefin compound of formula (III):

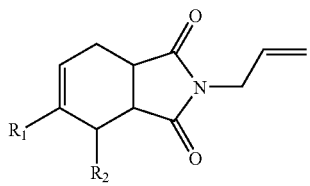

(wherein $R_1$ and $R_2$ each represents hydrogen, a C1-6 alkyl group, or a C1-4 trialkylsilyl group).

6. The process for production of an epoxy compound according to claim 5, wherein in formula (III), $R_1$ and $R_2$ are hydrogen, or $R_1$ is any one from among methyl, ethyl, propyl, isopropyl, tertiary butyl, trimethylsilyl, triethylsilyl and tertiary butyldimethylsilyl groups while $R_2$ is hydrogen, or $R_1$ is hydrogen while $R_2$ is any one of from among methyl, ethyl, propyl, isopropyl, tertiary butyl, trimethylsilyl, triethylsilyl and tertiary butyldimethylsilyl groups.

7. A process for production of an epoxy compound of claim 3 or 4, characterized by reacting a peroxide with an alicyclic olefin compound formula (IV):

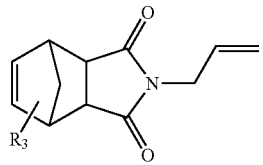

(wherein $R_3$ represents hydrogen, a C1-6 alkyl group, or a C1-4 trialkylsilyl group).

8. The process for production of an epoxy compound according to claim 7, wherein in general formula (IV), $R_3$ is hydrogen or any one from among methyl, ethyl, propyl, isopropyl, tertiary butyl, trimethylsilyl, triethylsilyl and tertiary butyldimethylsilyl groups.

\* \* \* \* \*